United States Patent [19]

Trees

[11] Patent Number: Plant 7,599

[45] Date of Patent: Jul. 23, 1991

[54] VARIETY OF GERANIUM NAMED PINK SATISFACTION

[75] Inventor: Scott C. Trees, Elburn, Ill.

[73] Assignee: Geo. J. Ball, Inc., West Chicago, Ill.

[21] Appl. No.: 519,299

[22] Filed: May 4, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new cultivar is characterized by its improved branching habit which provides more cuttings as well as by a fuller finished plant. It has very good keeping quality and high temperatures, wind and rain. It is also characterized by its delicate light pink color edged in white against a medium green foliage.

1 Drawing Sheet

BACKGROUND OF THE INVENTION

The present invention comprises a new and distinct cultivar of the *Pelargonium×hortorum* known by the varietal name Pink Satisfaction (Oglevee No. 1150, PAS No. GR-158C/85). The new variety was discovered in a selective breeding program by Mr. Scott Trees in April of 1985 in West Chicago, Ill. The new variety is a selection from the crossing of a single Salmon from $F_2$ Morgengrus by Pearl Necklace.

The new variety was first asexually reproduced by cuttings at Pan American Seed Company in West Chicago, Ill. following its discovery. The new variety has been repeatedly asexually reproduced by cuttings at Oglevee Ltd. in Connellsville, Pa. over a several year period. It has also been trial and field tested at Connellsville, Pa. during the summers of 1987, 1988 and 1989 and has been found to retain its distinctive characteristics through successive propagations.

The new variety has an improved branching habit providing more cuttings as well as a fuller finished plant. The new variety has shown very good keeping quality in high temperatures, wind and rain and is a substantial improvement over the current market variety "Pink Camilla" (unpatented).

The new cultivar when grown in a glass greenhouse in Connellsville, Pa. using natural light and 60° F. (night, 68° F. (day), and 71° F. (vent) has a response time of 6 weeks from a rooted cutting to flowering in a 10 centimeter pot. This response time was determined on plants grown in a soilless media employing constant fertilizer of 200 to 250 parts per million of nitrogen and potassium and in full light. The rooted cuttings were potted Aug. 1, 1989 and flowered Sept. 15, 1989.

DESCRIPTION OF THE DRAWING

FIG. 1 of the accompanying photographic drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected by asexual reproductions carried out by Oglevee Ltd. in Connellsville, Pa. The plant history was taken on six week plants blossomed under natural light in a greenhouse and color readings were taken indoors under 200–220 foot candles of cool, white fluorescent light. Color references are primarily to the R.H.S. Colour Chart of The Royal Horticultural Society of London.

THE PLANT

Classification:

*Botanical.*—*Pelargonium×hortorum.*

*Commercial.*—Zonal Florists Geranium.

Form: Bush; uniform mound.

Height: 20–22 cm above media surface.

Growth: Free and early flowering; good basal branching; vigorous, upright habit.

Strength: Stands upright without artificial support.

Foliage: Stalked leaf attachment; very faint zoning.

Leaves:

*Size.*—7.5–11 cm across (fully expanded leaf).

*Shape.*—Reniform; cordate base.

*Margin.*—Crenate.

*Texture.*—Leathery and slightly pubescent.

*Color.*—Top: Green Group 137C with a faint zone of Green Group 137B. Bottom: Green Group 138B.

Petioles: 7–9.5 cm in length; Yellow-Green Group 146B.

Stem:

*Color.*—Yellow-Green Group 146C.

*Internodes.*—1.5–3.0 in length.

THE BUD

Shape: Hemispherical cluster; individual bud is pointed and ovoid.

Size: 2.0–3.0 cm across.

INFLORESCENCE

Blooming habit: Semi-double; hemispherical.

Size: 9–10.5 cm when fully open.

Borne: Umbel; floret on pedicel; pedicel on peduncle; 5–8 cm above foliage canopy.

Florets:

*Form.*—Semi-double, flat to slightly cupped.

*Color.*—Top: Color washes from white at outer edges to Red Group 48D toward the center. Bottom: Red Group 49D.

*Petals.*—Obovate; not united, separate; margin entire; flat to slightly cupped; 7 to 8 in number.

*Size.*—4.0 to 4.5 cm across.

*Texture and appearance.*—Texture is smooth and satiny. Appearance from a distance is a delicate light pink edged in white with medium green foliage.

Petaloids:

*Quantity.*—None to 3.

*Shape.*—Twisted and elongated.

*Color.*—Red Group 48D.

Pedicel:

*Length.*—3.0 to 3.5 cm in length.

*Color.*—Base: Yellow-Green Group 146D (peduncle end). Tip: Yellow-Green Group 146D with a touch of Red-Purple.

Peduncle: Arises from the node, opposite leaf petiole.

*Color.*—Yellow-Green Group 146C.

*Length.*—14 to 17 cm.

Disease resistance: Not known.

Lasting quality: It has continually shown very good keeping quality in high temperatures, wind and rain during outdoor testing during the summers of 1987, 1988 and 1989.

REPRODUCTIVE ORGANS

Stamens:

*Anthers.*—2 mm in length; 5-7 in number.

*Filaments.*—5-7 mm in lengths; white to pale pink in color.

*Pollen.*—Golden brown.

Pistils:

*Number.*—1.

*Length.*—9-10 mm.

*Stigma.*—1; 5-7 parted, Red-Purple Group 58A.

*Style.*—3-5 mm in length.

Ovaries: Superior; pale green; very pubescent; 4-5 mm in length.

Fruit: None observed.

The new cultivar is characterized by its delicate light pink color edged in white with medium green foliage. It is further characterized by its good keeping quality in high temperatures, wind and rain as well as its better branching habit which provides more cuttings. It is also characterized by a fuller finished plant.

I claim:

1. A new and distinct variety of Geranium plant substantially as shown and described.

* * * * *

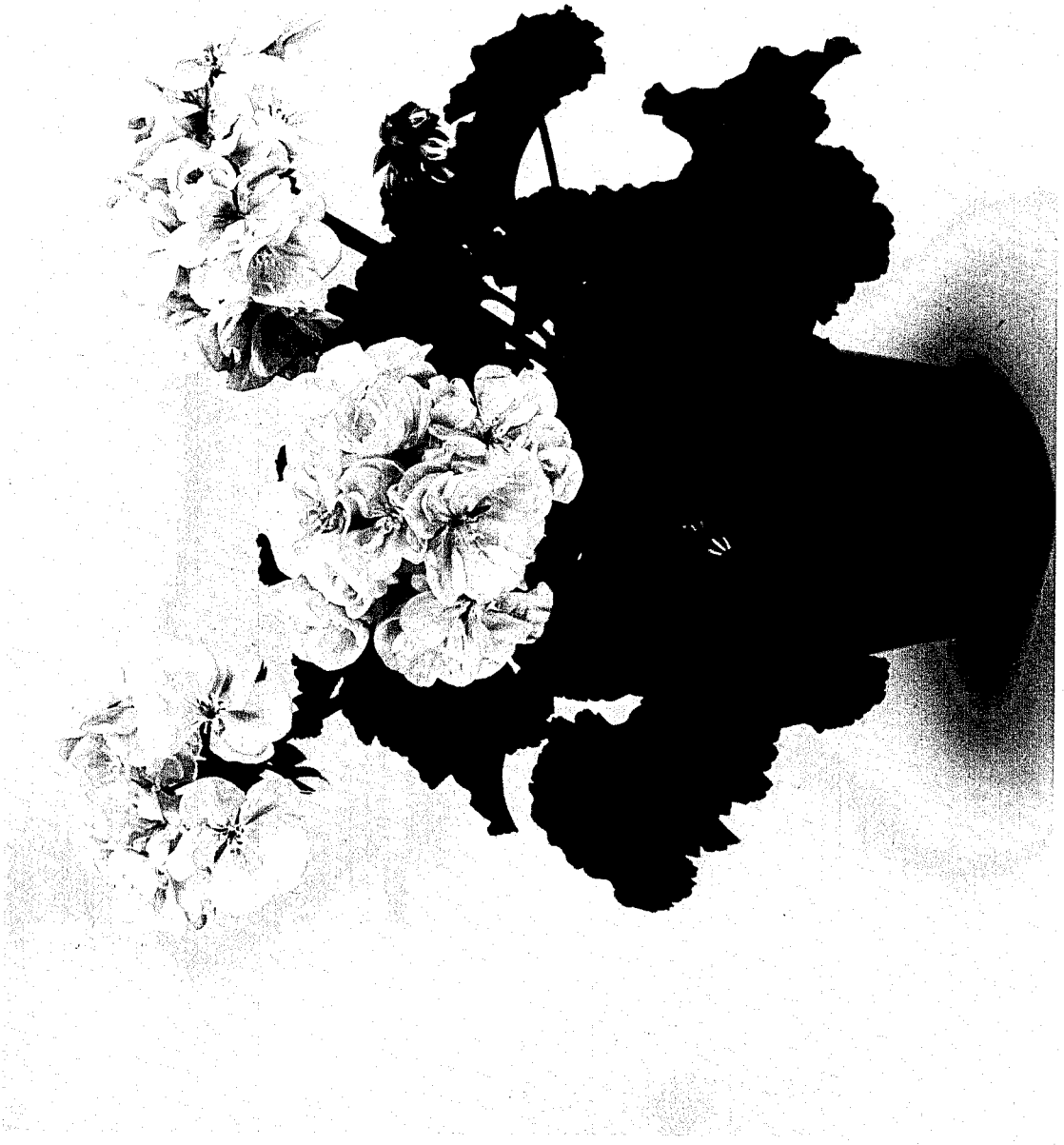

UNITED STATES PATENT AND TRADEMARK OFFICE

CERTIFICATE OF CORRECTION

PATENT NO. : Plant 7,599

DATED : July 23, 1991

INVENTOR(~~S~~) : Scott C. Trees

It is certified that error appears in the above-identified patent and that said Letters Patent is hereby corrected as shown below:

On the title page, item [57]:
Abstract Line 4 "and high" should read --in high--.

Column 1 Line 28 "(night" should read --(night)--.

Signed and Sealed this

Eleventh Day of August, 1992

*Attest:*

DOUGLAS B. COMER

*Attesting Officer*

*Acting Commissioner of Patents and Trademarks*